United States Patent [19]

Cohen et al.

[11]B 4,026,905

[45] May 31, 1977

[54] ELECTRICALLY CONDUCTING ORGANIC SALTS

[75] Inventors: Morrel H. Cohen, Chicago, Ill.; Malcolm G. Miles, Ladue; James D. Wilson, University City, both of Mo.

[73] Assignee: Monsanto Company, St. Louis, Mo.

[22] Filed: Dec. 26, 1972

[44] Published under the Trial Voluntary Protest Program on Jan. 28, 1975 as document No. B 318,122

[21] Appl. No.: 318,122

[52] U.S. Cl. .......................... 260/327 M; 252/500; 136/236R
[51] Int. Cl. .......................................... C07d 71/00
[58] Field of Search ................ 260/327 U; 252/500

[56] References Cited

UNITED STATES PATENTS 3,781,281   12/1973   Hartzler .................. 260/240 F

OTHER PUBLICATIONS

Melby, Canadian J. of Chemistry, vol. 43, pp. 1448–53 (1965)

Wudl et al., Chemical Communications, pp. 1453–4 (1970)

Heeger et al., "Magnetic Properties of Conducting Organic Salts", presented at the 18th Annual Conf. on Magnetism and Magnetic Materials, Nov. 28– Dec. 1, 1972, Denver, Colo., Abstract 7A–2

Perlstein et al., "Electron Transport and Magnetic Properties of a New Highly Conducting TCNQ Complex" presented at the 18th Annual Conference on Magnetism and Magnetic Materials," Nov. 28– Dec. 1, 1972, Denver, Colo., Abstract 7C–2 published in full by the AMERICAN INSTITUTE OF PHYSICS, AIP Conference Proceedings, No. 10, part 2, pp. 1494–98 (1973)

*Primary Examiner*—Henry R. Jiles
*Assistant Examiner*—C. M. S. Jaisle
*Attorney, Agent, or Firm*—Henry Craskell

[57] ABSTRACT

Compounds having a cation which is tetrathiafulvalene of 2,5-cyclohexadiene-1,4-diylidene-bis-1,3-dithiole or both, and an anion which is 7,7,8,8-tetracyano-p-quinodimethane or 11,11,12,12-tetracyano-2,6-naphthaquinonedimethane or both, are described. The above compounds are characterized by anions and cations which are both odd-electron species.

5 Claims, No Drawings

3,026,905

ELECTRICALLY CONDUCTING ORGANIC SALTS

DESCRIPTION OF PRIOR ART

The prior art is replete with references to a wide variety of electrically conducting organic compounds. Few of these have desirable combinations of electrical and thermal properties. One important class are salts containing both an organic anion as well as an organic cation. One specific class consists of these organic salts where both the anion and the cation are odd electron ions. By "odd electron ion" is meant an ion which contains an uneven number of bound electrons in the ion.

There are a number of references reporting the preparation of electrically conductive organic salts having a 7,7,8,8-tetracyano-p-quinodimethane anion,

hereinafter referred to as (TCNQ)$^-$. The best electrical conductivities reported so far for (TCNQ)$^-$ salts range up to about $10^2$ ohm$^{-1}$ cm$^{-1}$ for single crystals. Compacted crystals of (TCNQ)$^-$ salts have reported conductivities not exceeding about 5 ohm$^{-1}$ cm$^{-1}$.

Another anion which has been used in investigations of conductive organic salts is 11,11,12,12-tetracyano-2,6-naphthaquinodimethane,

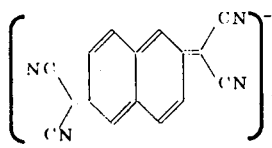

The ion 11,11,12,12-tetracyano-2,6-naphthaquinodimethane is referred to hereafter as (TNAP)$^-$. (TNAP)$^-$ salts have maximum reported conductivities of about $10^{-1}$ ohm$^{-1}$ cm$^{-1}$ for compacted crystals. No conductivities have been reported for single crystals of (TNAP)$^-$.

One specific cation which has been used in investigations relating to conductive organic salts has been tetrathiafulvalene

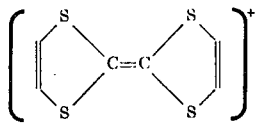

Tetrathiafulvalene will be referred to hereafter as (TTF)$^+$. Conductive (TTF)$^+$ organic salts have conductivities limited to about 2 ohm$^{-1}$ cm$^{-1}$ for compacted crystals. No conductivities have been reported for single crystals of any (TTF)$^+$ salt.

As far as has been determined, no electrically conductive organic salts have been reported having as a cation 2,5-cyclohexadiene-1,4-diylidene-bis-1,3-dithiole,

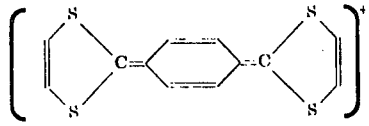

The ion 2,5-cyclohexadiene-1,4-diylidene-bis-1,3-dithiole is referred to hereinafter as (CHDT)$^+$.

This invention pertains to novel compositions of matter having electrically conductive properties. The novel compositions are characterized by organic anions and organic cations where both the anions and cations are odd electron species.

Summary of the Invention

This invention pertains to novel compositions of matter of formula $$A^+B^-$$

where A is

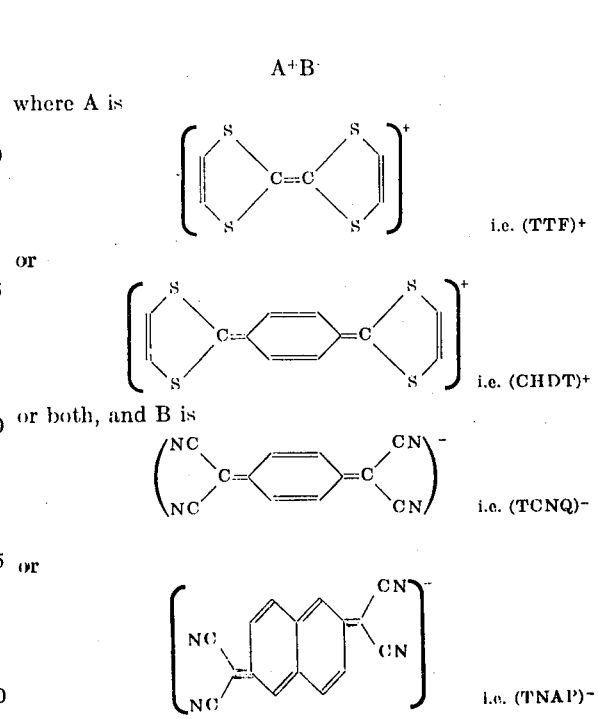

or both, and B is

DESCRIPTION OF THE PREFERRED EMBODIMENTS

Compounds of the above generic class are (tetrathiafulvalene)$^+$ (7,7,8,8-tetracyano-p-quinodimethane)$^-$, i.e. (TTF)$^+$ (TCNQ)$^-$;
(tetrathiafulvalene)$^+$ (11,11,12,12-tetracyano-2,6-naphthaquinodimethane)$^-$,
i.e. (TTF)$^+$ (TNAP)$^-$;
(2,5-cyclohexadiene-1,4-diylidene-bis-1,3-dithiole)$^+$ (7,7,8,8-tetracyano-p-quinodimethane)$^-$,
i.e. (CHDT)$^+$ (TCNQ)$^-$; and
(2,5-cyclohexadiene-1,4-diylidene-bis-1,3-dithiole)$^+$ (11,11,12,12-tetracyano-2,6-naphthaquinodimethane)$^-$
i.e. (CHDT)$^+$ (TNAP)$^-$.

In addition to any of the above compounds in pure form, the invention also comprises compositions of any one of the compounds with one or more of the remaining three. The compositions can contain the compounds in any proportion, for example with a binary system, from less than 1:10$^{-3}$ up to 1:1. For compositions containing more than two compounds, the individual compounds can similarly be present in any ratio anging from very small amounts of one, two or three compounds to compositions containing equimolar quantities of the compounds present in the composition. Preferred compositions have a preponderance of one compound with a minority of one or more other compounds present. As an example, compositions containing at least 80 mole percent of one compound with not more than 20 mole percent, preferably not more than 10 mole percent, of other component compounds are particularly useful. Examples of some compositions include 2 mole percent of $(TTF)^+$ $(TCNQ)^-$ and 98 percent of $(TTF)^+$ $(TNAP)^-$; one percent of $(TTF)^+$ $(TCNQ)^-$ and 99 percent of $(CHDT)^+$ $(TNAP)^-$; and two percent of $(TTF)^+$ $(TCNQ)^-$, six percent of $(CHDT)^+$ $(TCNQ)^-$ and 92 percent of $(CHDT)^+$ $(TNAP)^-$.

The compositions can be simple mixtures of the above crystalline compounds, as well as compositions in the form of a crystalline product where individual multiple anions and/or cations are present in the same crystal lattice. Preparation of a composition composed of different crystalline compounds by precipitation from a solution will result in the formation of a crystalline product where individual crystals contain a mixture of multiple anions and/or cations present, or a mixture of crystals of the individual compounds or both.

In addition to the above described compounds and compositions thereof, homologs and other simple derivatives of the compounds can also be employed, either as impurities in small quantity with the unsubstituted compound, as principal components of a composition, or as a pure compound. Suitable substituents include monovalent hydrocarbon groups such as methyl, ethyl, vinyl and phenyl groups and halogens such as chloro or bromo groups.

The compounds and compositions of this invention can be prepared by combining two or more electrically neutral reactants, or by combining two or more reactants which contain one or more of the desired ions. This can be accomplished by combining electrically neutral compounds such as (TTF) and (TCNQ) in an appropriate medium to produce $(TTF)^+$ $(TCNQ)^-$. Alternatively, a compound containing one of the ions in its ionic form such as $(TTF)^+$ iodide or sodium $TNAP)^-$ can be reacted either with an electrically neutral compound or with another ionic salt which can supply the necessary ion of opposite charge to form the compounds of this invention. The materials containing the desired compound components are usually brought together in the presence of a suitable solvent for the reactants such as acetonitrile, methylene chloride or acetone or a mixture of solvents such as acetonitrile-methanol, acetone-water-methanol and the like. Thorough contact of neat reactants, such as can be attained in the vapor phase, in the absence of any solvent or dispersing medium can also be used to form the compounds or compositions of this invention. If the reactants are salts having ions, such as iodine, sodium, nickel or hexafluoroantimonate, which are not to become part of the compounds or compositions of this invention, the reaction mixture can be purified through crystallization or other known techniques to remove the byproducts of the reaction. Reaction temperatures are usually about 0° to 150°C, preferably about 20° to 50°C. For convenience it can vary considerably depending upon the thermal stability of the reactants and the time alloted for the reaction. One suitable combination of reaction time and temperature which has been employed because of its convenience has been 20° to 25°C for 2 or 3 days. The 2 or 3 day reaction period is principally a matter of convenience, however, and can be shortened considerably with little or no loss in yield.

The compounds and compositions of this invention are useful as electrical conductors. Because of their advantageous combination of properties such as thermal and electrical conductivities and thermoelectric power coefficient, they are particularly useful as thermoelectric elements in thermoelectric devices. Compacted crystals of compounds or compositions of this invention have electrical conductivities at least an order of magnitude higher than conductivities reported in the prior art. Similarly, compounds of compositions of this invention in single crystal form also exhibit higher electrical conductivities than reported in the prior art for single crystals of related compounds.

EXAMPLE 1

$(TTF)^+$ $(TCNQ)^-$ is prepared by dissolving 0.1 millimole of $(TTF)^+$ iodide in 100 ml. of acetonitrile and adding the resultant solution to a solution of 0.1 millimole of (TCNQ) in 50 ml. of acetonitrile. The resultant reaction mixture is filtered after three days to give a 50 percent yield of a black microcrystalline product. Calculated elemental analysis for $(TTF)^+$ $(TCNQ)^-$, $C_{18}H_8N_4S_4$ is C, 52.92%; H, 1.97%; N, 13.40%. Found: C, 52.70%; H, 1.95%; N, 13.81%.

The compound is compacted at 90,000 psi in a microdie, and volume resistivity measured by the 4-probe technique is found to be $5 \times 10^{-2}$ ohm cm. Seebeck coefficient is $-26$ microvolts $deg^{-1}$; thermal conductivity is $2 \times 10^{-3}$ watts $cvs^{-1}$ $deg^{-1}$.

EXAMPLE 2

$(TTF)^+$ $(TCNQ)^-$ is prepared by dissolving two millimoles of $(TTF)^+$ $(SbF_6)^-$ in 25 ml. of acetonitrile and adding the resultant solution to a solution containing 2 millimoles of $Li^+$ $(TCNQ)^-$ in 25 ml. of methanol. The resultant reaction mixture is filtered after two days to give a 55 percent yield of a black microcrystalline product, tentatively identified as $(TTF)^+$ $(TCNQ)^-$. Elemental analysis for $(TTF)^+$ $(TCNQ)^-$, $C_{18}H_8N_4S_4$ is calculated to be C, 52.92%; H, 1.97%; N, 13.40%. Found: C, 52.91%; H, 1.91%; N, 13.64%. Volume resistivity for the compacted polycrystalline material is $2 \times 10^{-2}$ ohm cm. Seebeck coefficient is $-22$ microvolts $deg^{-1}$.

EXAMPLE 3

$(TTF)^+$ $(TCNQ)^-$ is prepared by dissolving 10 millimoles of (TTF) in 200 ml. of acetonitrile and adding the resultant solution to a solution containing 10 millimoles of (TNCQ) in 400 ml. of a 3:1 solution of methylene chloride and acetonitrile. The reaction mixture is allowed to stand for seven hours and filtered after that time to give a 50 percent yield of a black microcrystalline product, tentatively identified as $(TTF)^+$ $(TCNQ)^-$. Elemental analysis calculated for $C_{18}H_8N_4S_4$ is C, 52.92%; H, 1.97%; N, 13.40%. Found: C, 52.70%; H, 2.03%; N, 13.58%. The volume resistivity is $1 \times 10^{-2}$ ohm cm. Seebeck coefficient is $-20$ microvolts $deg^{-1}$.

EXAMPLE 4

A sample of $(TTF)^+$ $(TCNQ)^-$ prepared according to the procedure of Example 3 is crystallized from warm dimethyl formamide. The material crystallized as black rectangular plates opaque in reflected light and yellow-green in transmitted light. Volume resistivity in the long axis of the plates measured by the 4-probe technique is found to be in the range 1.4 to 3.5 ×10⁻³ ohm cm. Seebeck coefficient is in the range −20 to −30 microvolts deg⁻¹. X-ray analysis shows the crystal to have the space group P2₁/C. Unit cell dimensions are $a = 12.25$ A; $b = 3.81$ A; $C = 9.20$ A; $\beta = 105°$ with two molecules in the unit cell.

EXAMPLE 5

(TTF)⁺ (TNAP)⁻ is prepared by dissolving 1 millimole of (TTF) in 20 ml. of acetonitrile warmed to about 40°C, and adding the resultant solution to a solution of 500 ml. of boiling acetonitrile containing 1 millimole of (TNAP). The solution is set aside and allowed to cool overnight, after which time the solution is filtered to give a 70 percent yield of a black microcrystalline product identified as (TTF)⁺ (TNAP)⁻. Volume resistivity is 1 × 10⁻² ohm cm. Seebeck coefficient is −22 µ volts deg⁻¹.

EXAMPLE 6

To a separatory funnel containing 100 parts deoxygenated methylene chloride and 100 parts of a 0.1 molar solution of sodium bi-sulfite in deoxygenated water is added a suspension of 5 parts 1,4-phenylene-bis-2(1,3-dithiolium) difluoroborate in 20 parts acetonitrile. The mixture is agitated for 15 minutes by bubbles of nitrogen gas, after which time the mixture is allowed to settle, thereby permitting the layers to separate. The methylene chloride solution is withdrawn and the aqueous layer washed with an additional 100 parts of methylene chloride. The combined methylene chloride solutions are dried and evaporated under reduced pressure, leaving a residue which is recrystallized from CCl₄-ethanol, and identified as 2,5-cyclohexadiene-1,4-diylidene bis-1,3-dithiole, i.e., (CHDT).

EXAMPLE 7

One equivalent of (CHDT) and one equivalent of 1,4-phenylenebis-2(1, 3-dithiolium) difluoroborate are dissolved in 100 parts dry acetonitrile, giving a deep red solution of 2 parts (CHDT)⁺ BF₄⁻. To this is added a hot solution of 2 parts lithium (TNAP) in methanol. On cooling black crystals of (CHDT)⁺ (TNAP)⁻ appear which are collected by suction filtration.

EXAMPLE 8

A solution of potassium sulfide in ethanol is prepared by dissolving 40 parts potassium hydroxide in 250 parts absolute ethanol, saturating this solution with hydrogen sulfide, and then dissolving in this solution an additional 40 parts of potassium hydroxide. The solution is allowed to cool, and 20 parts of a, a, a, a', a', a'-hexachloro-p-xylene is added, with stirring. The resulting mixture is heated slowly to 45°, and kept at that temperature for 2 hours. The temperature is then raised to reflux, where it is allowed to remain for an additional three hours. The solution is filtered while hot and allowed to cool, whereupon crystals of the red dipotassium tetrathioterephthalate appear. This salt (11 parts) is collected by filtration.

Bromoacetaldehyde (10 parts) is added slowly to a suspension of 5 parts dipotassium tetrathiotherephthalate in 150 parts cold (0°C) ethanol; the resulting red solution is allowed to warm to 25°, and is stirred for an hour. It is filtered, and the filtrate is cooled in ice and saturated with hydrogen sulfide. To this solution is then added 10 parts aqueous fluoroboric acid. The mixture is allowed to react for four hours. Crystals of 1,4-phenylenebis-2(1,3-dithiolium) difluoroborate (2 parts) are then collected by filtration and washed with 20 parts 1:1 ethanol-ether.

To a solution of ten parts of 1,4-dilithiobenzene prepared from 1,4-dibromobenzene and n-buthyl lithium, as described by Nielsen and McEwen (J. Am. Chem. Soc. 79, 3081 (1957), is added solid 2-methylthio-1,3-dithiolium iodide (20 parts) in small portions. The dark solution slowly lightens, eventually attaining a yellow-brown coloration. After the reaction is complete, the solvent is evaporated and the residual gum treated with a mixture consisting of 100 parts deaerated water and 100 parts dichloromethane. The aqueous layer is washed once with dicloromethane and discarded. The combined dichloromethane solutions are evaporated and the tan residue treated with six parts of 2,3-dichloro-5,6-dicyano-1,4-benzoquinone (DDQ) dissolved in boiling dichloromethane. After one-half hour the blue-black solid is recovered by filtration, giving one part product identified as (CHDT)⁺ (DDQ)⁻.

Equimolar parts of (CHDT)⁺ (DDQ)⁻ and lithium (TCNQ)⁻ are added to hot acetonitrile and the resultant solution is stirred for 2 hours, after which time it is permitted to cool to room temperature. The solution is filtered and the black crystalline precipitated product is identified as (CHDT)⁺ (TCNQ)⁻.

EXAMPLE 9

A mixture of (TTF)⁺ (TNAP)⁻ and (TTF)⁺ (TCNQ)⁻ is prepared by dissolving 1 millimole of (TTF) in 20 ml of acetonitrile and adding the resultant solution to a solution of 500 ml. of hot acetonitrile containing 0.8 millimole of (TNAP) and 0.2 millimole of (TCNQ). The solution is allowed to cool overnight, after which time the solution is filtered to give a 70 percent yield of the black microcrystalline product mixture, (TTF)⁺ (TNAP)⁻ and (TTF)⁺ (TCNQ)⁻.

We claim:
1. A compound of the formula A⁺ B⁻ where A is

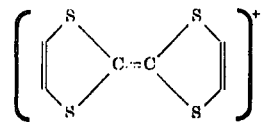

or

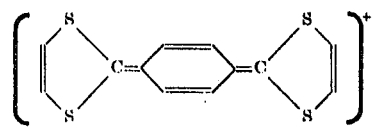

and B is

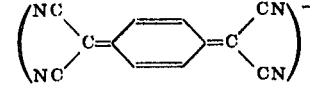

or

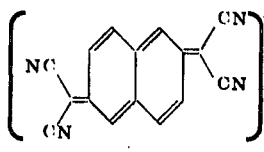

2. (Tetrathiafulvalene)⁺ (7,7,8,8-tetracyano-p-quinodimethane)⁻.

3. (Tetrathiafulvalene)$^+$ (11,11,12,12-tetracyano-2,6-naphthaquinodimethane)$^-$.

4. (2,5-Cyclohexadiene-1,4-diylidene-bis-1,3-dithiole)$^+$ (7,7,8,8-tetracyano-p-quinodimethane)$^-$.

5. (2,5-Cyclohexadiene-1,4,-diylidene-bis-1,3-dithiole)$^+$ (11,11,12,12-tetracyano-2,6-naphthaquinodimethane)$^-$.

* * * * *